US008994941B2

(12) United States Patent
Shi (10) Patent No.: US 8,994,941 B2
(45) Date of Patent: Mar. 31, 2015

(54) OPTICAL SYSTEM, APPARATUS AND METHOD FOR PERFORMING FLOW CYTOMETRY

(71) Applicant: General Electric Company, Schenectady, NY (US)

(72) Inventor: Xiaolei Shi, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/687,374

(22) Filed: Nov. 28, 2012

(65) Prior Publication Data

US 2014/0146316 A1 May 29, 2014

(51) Int. Cl.
G01N 21/00 (2006.01)
G01N 21/53 (2006.01)
G01N 21/64 (2006.01)

(52) U.S. Cl.
CPC ............... *G01N 21/53* (2013.01); *G01N 21/64* (2013.01)
USPC .......................................... 356/342; 356/340

(58) Field of Classification Search
USPC ............... 356/335–343, 73, 39, 72, 317, 318, 356/326, 40, 432–444
See application file for complete search history.

(56) References Cited

U.S. PATENT DOCUMENTS

| | | | |
|---|---|---|---|
| 4,415,265 A * | 11/1983 | Campillo et al. | 356/338 |
| 5,260,764 A | 11/1993 | Fukuda et al. | |
| 6,597,438 B1 | 7/2003 | Cabuz et al. | |
| 6,947,127 B2 | 9/2005 | Wolleschensky et al. | |
| 7,075,647 B2 | 7/2006 | Christodoulou | |
| 7,463,344 B2 | 12/2008 | Wolleschensky et al. | |
| 7,800,754 B2 | 9/2010 | Kenyon | |
| 7,843,563 B2 | 11/2010 | Fritz et al. | |
| 8,108,031 B2 | 1/2012 | Georgakoudi et al. | |
| 2009/0142765 A1 | 6/2009 | Vacca et al. | |
| 2010/0220315 A1 | 9/2010 | Morrell et al. | |
| 2011/0090500 A1 | 4/2011 | Hu et al. | |
| 2011/0261446 A1 | 10/2011 | Dunsby et al. | |
| 2012/0050738 A1 | 3/2012 | Swalwell | |

FOREIGN PATENT DOCUMENTS

WO 2009/095679 A2 8/2009

OTHER PUBLICATIONS

Mao et al., "An Optofluidic Approach to Miniature Flow Cytometry", IEEE Winter Topicals (WTM), Jan. 10-12, 2011.
PCT International Search Report and Written Opinion from corresponding PCT Application No. PCT/US2013/062555 dated Feb. 27, 2014.

* cited by examiner

*Primary Examiner* — Tri T Ton
(74) *Attorney, Agent, or Firm* — Jason K. Klindtworth (57) ABSTRACT

An optical system includes a radiation source, a radiation-illuminating device, and a radiation-collecting device. The radiation source is configured to generate radiation. The radiation-illuminating device is optically coupled to the radiation source and configured to direct and focus the radiation obliquely with respect to an optical axis thereof onto a sample. The radiation-collecting device is configured to collect back-scattered radiation scattered from the sample and spatially separated from noise radiation. Associated apparatus and method are also described.

17 Claims, 11 Drawing Sheets

OPTICAL SYSTEM, APPARATUS AND METHOD FOR PERFORMING FLOW CYTOMETRY

STATEMENT REGARDING FEDERALLY SPONSORED RESEARCH & DEVELOPMENT

This invention was made with Government support under contract number N00173-08-2-0003 that was awarded by the Navel Research Laboratory. The Government has certain rights in the invention.

BACKGROUND

Embodiments of the invention relate generally to an optical system, an apparatus and a method, and more particularly to an optical system, an apparatus and a method for performing flow cytometry.

An apparatus for performing flow cytometry generally counts, measures and discriminates particles in a liquid by their optical properties as they are illuminated by radiation. The particles are normally prepared by labeling them with one or more fluorescent markers. Each fluorescent marker emits radiation of a characteristic wavelength range when it is excited by the radiation. It is common to detect the forward-scattering radiation scattered from the illuminated particle to obtain one or more characteristics of the particle. Accordingly, some optical elements of the apparatus are positioned at the back side of the particles to illuminate the particles, and some optical elements of the apparatus are positioned at the front side of the particles to collect the forward-scattering radiation. The optical elements are arranged at both sides of the particles, so that the arrangement of the apparatus is not compact, which is not suitable for point-of-care applications.

It is desirable to provide an optical system, an apparatus and a method to address the above-mentioned problem.

BRIEF DESCRIPTION

In accordance with one embodiment disclosed herein, an optical system is provided. The optical system includes a radiation source, a radiation-illuminating device, and a radiation-collecting device. The radiation source is configured to generate radiation. The radiation-illuminating device is optically coupled to the radiation source and configured to direct and focus the radiation obliquely with respect to an optical axis thereof onto a sample. The radiation-collecting device is configured to collect back-scattered radiation scattered from the sample and spatially separated from noise radiation.

In accordance with another embodiment disclosed herein, an apparatus is provided. The apparatus includes an optical system and a detector. The optical system is configured to illuminate a sample obliquely with respect to an optical axis thereof and spatially separate noise radiation from back-scattered radiation scattered from the sample. The detector is optically coupled to the optical system to detect the back-scattered radiation from the optical system.

In accordance with another embodiment disclosed herein, a method is provided. The method includes illuminating a sample with an oblique incidence beam inclined with respect to an optical axis of an optical system. The method further includes spatially filtering noise radiation from back-scattered radiation scattered from the sample. The method further includes detecting the back-scattered radiation.

DRAWINGS

These and other features and aspects of the present invention will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a", "an" and "one" do not denote a limitation of quantity, but rather denote the presence of at least one of the referenced items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical or optical connections or couplings, whether direct or indirect. For illustration purpose only, radiation is illustrated by lines along axes of actual radiation which has widths.

Figure 1:
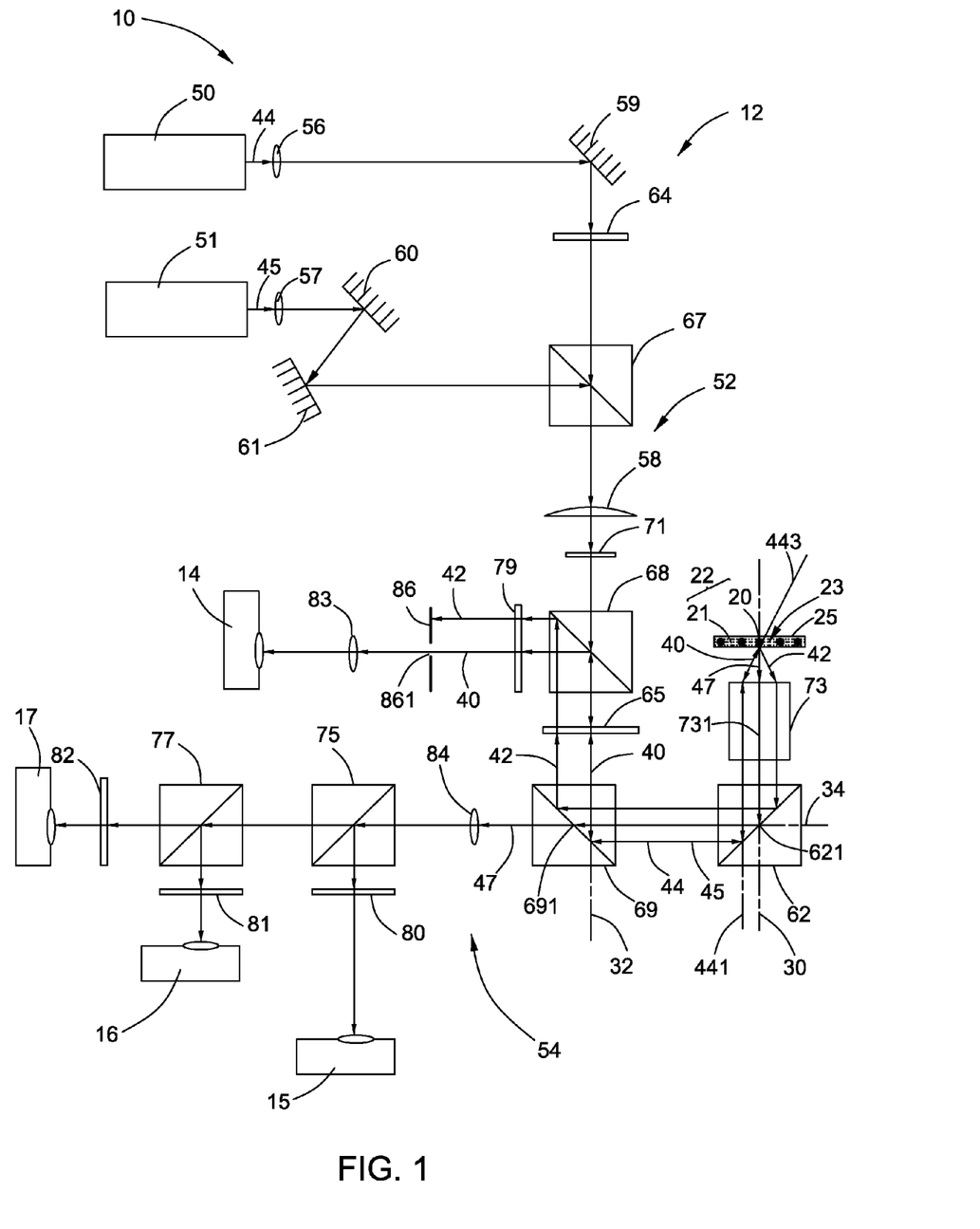
FIG. 1 is a schematic view of an apparatus for performing flow cytometry in accordance with an exemplary embodiment.

FIG. 1 illustrates a schematic view of an apparatus 10 for performing flow cytometry in accordance with an exemplary embodiment. The apparatus 10 is configured to collect and detect back-scattered radiation 40 scattered from a sample 22. The sample 22, in this embodiment, contains one or more particles 20, such as fluorescent beads, present in background matrices 21, such as buffered water. The particles 20 are irradiated while passing through an interrogation zone 23 of a flow cell in a transparent chip 25. The apparatus 10 includes an optical system 12 and detectors 14-17 optically coupled to the optical system 12.

The optical system 12 is configured to illuminate the sample 22 obliquely with respect to an optical axis 30 thereof and spatially separate noise radiation 42 from the back-scattered radiation 40. The noise radiation 42 mainly includes back-reflection noise beams from an outer surface of the chip 25 and interfaces of substrates (not shown) of the chip 25. The optical system 12 includes radiation sources 50, 51, a radiation-illuminating device 52 and a radiation-collecting device 54.

The radiation sources 50, 51 are configured to generate radiation 44, 45 to illuminate the particles 20. The radiation 44, 45 has at least one wavelength component, and more preferably two or more wavelength components. When multiple wavelength components are utilized, the radiation at these wavelengths can be performed simultaneously, or in separate temporal intervals. In the illustrated embodiment, two radiation sources 50 and 51 are provided to generate the radiation 44 and 45 in two separate wavelength regions. In this embodiment, the two radiation sources 50 and 51 respectively generate red radiation at a wavelength of about 637 nm and green radiation at a wavelength of about 532 nm. In another embodiment, the radiation at other wavelengths may be generated and utilized depending on the fluorescent molecule used. In some embodiments, a single radiation source may be provided to generate radiation having one or more wavelength components. The optical system 12 may include any number of radiation sources. In some embodiments, the radiation sources 50, 51 may be lasers, which include, but are not limited to, gas, diode and solid-state lasers, such as helium-neon or argon lasers. In other embodiments, the radiation sources 50 and 51 may be any other suitable radiation sources.

The radiation-illuminating device 52 is optically coupled to the radiation sources 50, 51 and configured to direct and focus the radiation 44, 45 obliquely with respect to the optical axis 30 thereof onto the particles 20. In this embodiment, the radiation-illuminating device 52 includes lenses 56-58, mirrors 59-62, wave plates 64 and 65, beam splitters 67, 68, a first beam splitter 69, a filter 71, and an objective lens 73. In this embodiment, the lenses 56 and 57 respectively collimate the radiation 44 and 45 emitted by the radiation sources 50 and 51 to generate collimated beams. The radiation 44 through the lens 56 is directed via the mirror 59 to the wave plate 64 that in turn passes the radiation 44 through to reach the beam splitter 67. The wave plate 64 changes the polarization of the radiation 44 to maximize the transmission through the beam splitters 67 and 68. The wave plate 64, in this embodiment, may be a half-wave plate. The radiation 45 through the lens 57 is directed via the mirrors 60 and 61 to reach the beam splitter 67. In this embodiment, the mirrors 59-61 are utilized to shift propagation directions of the radiation 44 and 45 so that optical elements including the radiation sources 50, 51 and the lens 56, 57 may be arranged compactly.

The beam splitter 67, in this embodiment, may be a dichroic beam splitter, which allows the radiation 44 to pass through while reflecting the radiation 45 in a direction that is substantially co-linear with that of the radiation 44 to generate a co-propagating beam containing wavelength components from both radiation sources 50 and 51. The radiation 44 and 45 are then transmitted through the lens 58 to the filter 71 that filters the radiation 44 and 45 to reduce leakage light background and make signals of the radiation 44 and 45 cleaner. The filter 71, in this embodiment, may be a band-pass filter. The lens 58 is a cylindrical lens to form a line focus at the sample 22. The radiation 44 and 45 passing through the filter 71 are transmitted to the beam splitter 68. The beam splitter 68, in this embodiment, may be a polarizing beam splitter, which allows the radiation 44 and 45 to pass through while reflecting the back-scattered radiation 40 and the noise radiation 42. The radiation 44 and 45 from the beam splitter 68 are transmitted through the wave plate 65 which, in this embodiment, may be a quarter-wave plate, to the first beam splitter 69. The wave plates 64, 65, the beam splitters 67, 68, the lens 58 and the filter 71 are aligned along an optical axis 32 of the radiation-illuminating device 52, and the radiation 44 and 45 from the beam splitter 67 are transmitted along the optical axis 32 through the lens 58, the filter 71, the beam splitter 68 and the wave plate 65.

At least one of the first beam splitter 69 and the mirror 62 is regarded as a radiation-shift element which shifts the radiation 44 and 45 and has a center distant from the optical axis of the radiation-illuminating device 52 to translate the radiation 44 and 45 from the optical axis of the radiation-illuminating device 52. In the illustrated embodiment, the first beam splitter 69 is the radiation-shift element optically coupled to the radiation sources 50 and 51. The first beam splitter 69 is configured to translate the radiation 44 and 45 and separate the back-scattered radiation 40 and fluorescence radiation 47 from the particles 20. The first beam splitter 69 has a center 691 distant from the optical axis 32 of the radiation-illuminating device 52. The radiation 44 and 45 from the wave plate 65 along the optical axis 32 are reflected via the first beam splitter 69 to the mirror 62. The radiation 44 and 45 are translated from an optical axis 34 of the radiation-illuminating device 52. The first beam splitter 69, in this embodiment, may be a dichroic beam splitter, which reflects the radiation 44 and 45 while allowing the fluorescence radiation 47 from the particles 20 to pass through.

The mirror 62 has a center 621 aligned with the optical axes 30 and 34 but distant from the radiation 44 and 45 projected to the mirror 62. The mirror 62 reflects the radiation 44 and 45 from the first beam splitter 69 to the objective lens 73. In some embodiments, a beam splitter may be used instead of the mirror 62 to reflect the radiation 44 and 45. The objective lens 73 has a lens axis 731 which, in this embodiment, is co-linear with the optical axis 30 of the radiation-illuminating device 52 and translated from a beam axis 441 of the radiation 44 and 45 projected thereto. The objective lens 73 focuses the radiation 44 and 45 obliquely with respect to the lens axis 731 and the optical axis 30 onto the particle 20 while the particle 20 passes through the interrogation zone 23. Accordingly, a beam axis 443 of the radiation 44 and 45 from the objective lens 73 is oblique with respect to the lens axis 731 and the optical axis 30. The radiation 44 and 45 each are focused at a center of the interrogation zone 23 which is substantially aligned with the optical axis 30.

The radiation-collecting device 54 is configured to collect the back-scattered radiation 40. The radiation-collecting device 54 includes the objective lens 73, the mirror 62, the first beam splitter 69, the wave plate 65, the beam splitter 68, beam splitters 75, 77, filters 79-82, lenses 83, 84, and a radiation limiting element 86. The back-scattered radiation 40 from the illuminated particle 20 is transmitted in a direction that is substantially co-linear with that of the radiation 44 and 45. The back-scattered radiation 40 has one or more wavelength components associated with scattering by the radiation 44 and 45. In the illustrated embodiments, the back-scattered radiation 40 includes red back-scattered radiation at a wavelength corresponding to that of a scattering by the red radiation 44 and green back-scattered radiation at another wavelength corresponding to that of a scattering by the green radiation 45.

The noise radiation 42 is mainly generated by the outer surface and the interfaces of the chip 25 which reflect the radiation 44 and 45, and spatially separated from the back-scattered radiation 40. The fluorescence radiation 47 from the illuminated particle 20 is emitted along the lens axis 731 of the objective lens 73. The fluorescence radiation 47 is emitted by the labeled particles, and more particularly their fluorescent labels which are excited by the radiation 44 and 45. The fluorescence radiation 47 has one or more wavelength components associated with excitation by the radiation 44 and 45.

The back-scattered radiation 40, the noise radiation 42 and the fluorescence radiation 47 are spatially separated from each other and emitted to the objective lens 73 that directs the back-scattered radiation 40, the noise radiation 42 and the fluorescence radiation 47 to the mirror 62. The back-scattered radiation 40, the noise radiation 42 and the fluorescence radiation 47 are then directed via the mirror 62 to the first beam splitter 69 that allows the passage of the fluorescence radiation 47 and reflects the back-scattered radiation 40 and the noise radiation 42. The back-scattered radiation 40 and the noise radiation 42 then pass through the wave plate 65 to the beam splitter 68 that in turn reflects the back-scattered radiation 40 and the noise radiation 42 to the filter 79.

The filter 79 allows the passage of the back-scattered radiation 40 in a wavelength region which may be detected, but substantially blocks the back-scattered radiation 40 in other wavelength regions. In the illustrated embodiment, the filter 79, which may be a band-pass filter, allows the passage of the red back-scattered radiation which may be detected to obtain the profile of the particles 20. In another embodiment, the filter 79 may allow the passage of the green back-scattered radiation but block the red back-scattered radiation. The filter 79 also blocks a portion of the noise radiation.

The radiation limiting element 86 allows the passage of the back-scattered radiation 40 and filters the noise radiation 42. The radiation limiting element 86 includes an aperture 861 allowing the back-scattered radiation 40 to pass through to spatially filter out the noise radiation 42 from the back-scattered radiation 40. The aperture 861 is positioned and dimensioned to let the back-scattered radiation 40 pass through. The aperture 861 may be a pinhole, slit, or any other forms allowing the passage of the back-scattered radiation 40. In the illustrated embodiment, the radiation limiting element 86 is located downstream of the filter 79. In another embodiment, the radiation limiting element 86 may be located upstream of the filter 79. The radiation limiting element 86 filters the noise radiation 42 from the back-scattered radiation 40, and then the back-scattered radiation 40 from the radiation limiting element 86 is filtered by the filter 79.

The lens 83 focuses the back-scattered radiation 40 from the radiation limiting element 86 onto the detector 14. The detector 14 may be a multi-element detector providing a beam spatial distribution image. The detector 14 may be a photo detector or an array of photo detectors or some other device. In some embodiments, the detector 14 may spatially filter the noise radiation 42 to detect the back-scattered radiation 40 while the radiation limiting element 86 is omitted.

In this embodiment, the fluorescence radiation 47 from the first beam splitter 69 is converged via the lens 84 to the beam splitter 75 that in turn reflects the fluorescence radiation 47 in a wavelength region and allows the fluorescence radiation 47 in other wavelength regions to pass through. The beam splitter 75 may be a dichroic filter. The fluorescence radiation 47 reflected by the beam splitter 75 is transmitted through the filter 80 onto the detector 15. The filter 80 may be a band-pass filter to filter out noises from the fluorescence radiation 47. The fluorescence radiation 47 passing through the beam splitter 75 is separated via the beam splitter 77 respectively to the filters 81 and 82 that in turn pass the fluorescence radiation 47 onto the detectors 16 and 17. The beam splitter 77 may be a dichroic filter. The filters 81 and 82 may also be band-pass filters to filter out noises from the fluorescence radiation 47.

The detectors 15-17 may be photomultiplier tubes (PMT), avalanche photodiodes (APD) or other suitable detectors. The detectors 14-17 transmit detected signals to an analysis module (not shown) such as a computer on which software for analysis of the data of the detected signals.

In the embodiment shown in FIG. 1, the radiation source 50, 51, the radiation-illuminating device 52, the radiation-collecting device 54 and the detectors 14-17 are arranged at a single side of the chip 25 so that the apparatus 10 has a compact arrangement. The radiation 44 and 45 illuminate the sample 22 from a bottom side of the chip 25 and the back-scattered radiation 40 is also collected from the bottom side of the chip 25. Accordingly, in this embodiment, there are no optical elements at a top side of the chip 25, so that it is easy to change the chip 25 from the top side. In some embodiments, one or more optical elements shown in FIG. 1, such as the mirrors 59-61, the lens 58, the filters 71, 79, the radiation limiting element 86 and so on, may be optional or replaced by any other optical elements having similar functions. In some embodiments, one or more of other optical elements, such as mirrors, beam splitter and so on, may be utilized in the apparatus 10.

Figure 2:
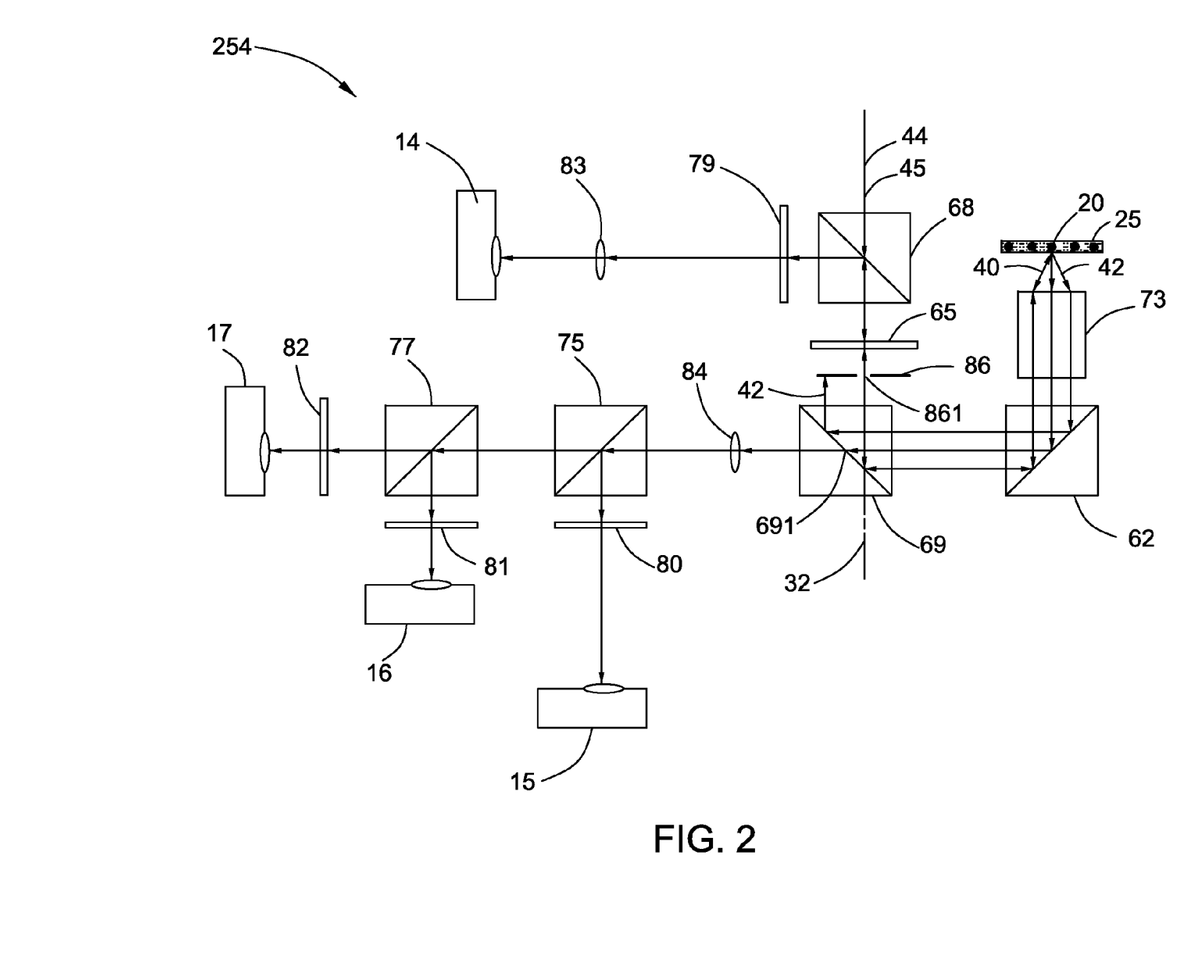
FIG. 2 is a schematic view of a radiation-collecting device of an apparatus in accordance with another exemplary embodiment.

FIG. 2 illustrates a schematic view of a radiation-collecting device 254 in accordance with another exemplary embodiment. The radiation-collecting device 254 in this embodiment may be operated in a manner similar to the radiation-collecting device 54 of the embodiment in FIG. 1. Compared with the embodiment of FIG. 1, the radiation limiting element 86 in FIG. 2 is located between the beam splitter 68 and the first beam splitter 69. In this embodiment, the radiation limiting element 86 may be located between the wave plate 65 and the first beam splitter 69. In another embodiment, the radiation limiting element 86 is located between the beam splitter 68 and the wave plate 65, or any other suitable positions. In the illustrated embodiment, the aperture 861 of the radiation limiting element 86 is aligned with the radiation 44 and 45 and dimensioned to let the radiation 44, 45 and the back-scattered radiation 40 pass through. The noise radiation 42 is blocked via the radiation limiting element 86.

Figure 3:
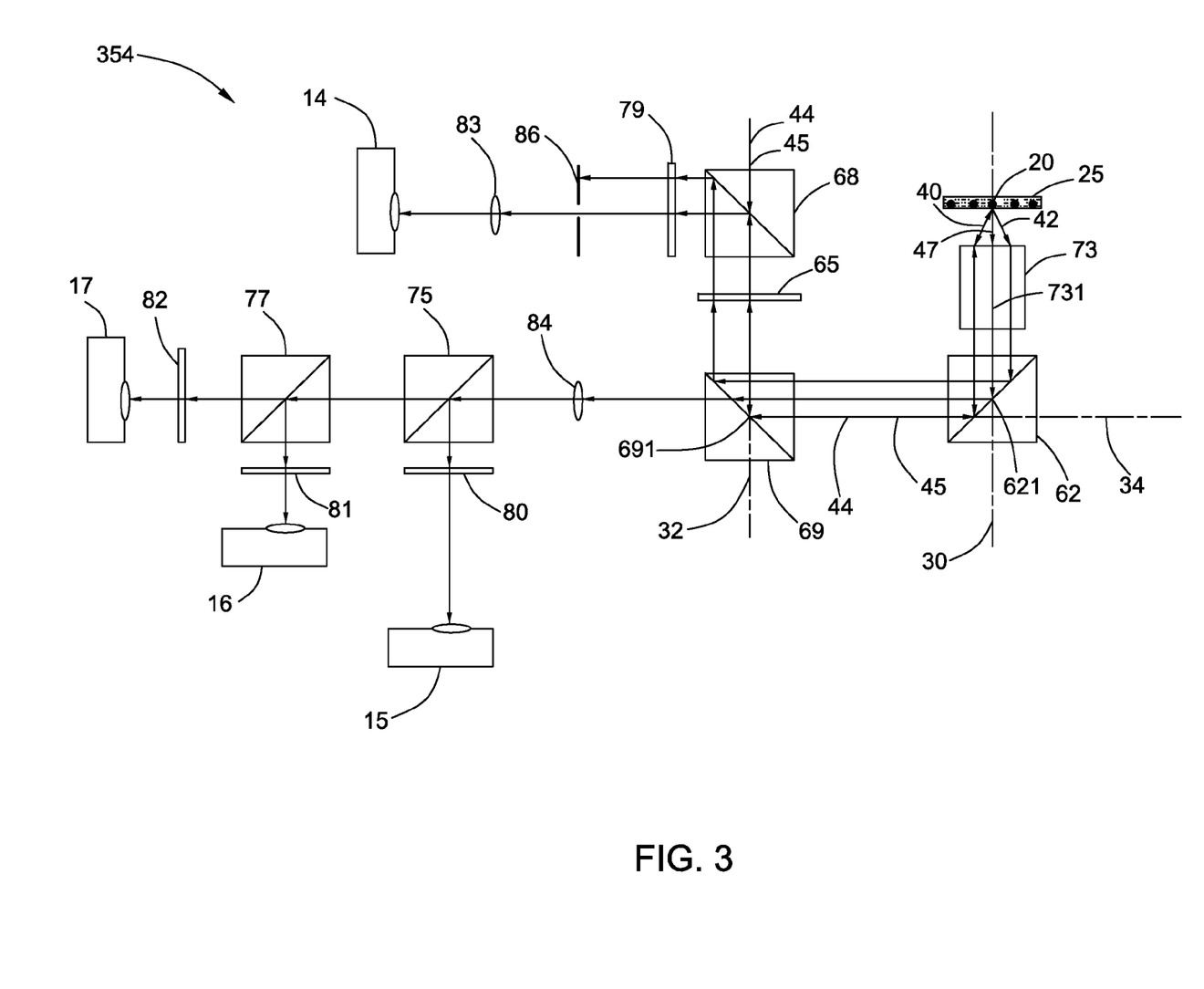
FIG. 3 is a schematic view of a radiation-collecting device in accordance with another exemplary embodiment.

FIG. 3 illustrates a schematic view of a radiation-collecting device 354 in accordance with another exemplary embodiment. The radiation-collecting device 354 in this embodiment may be operated in a manner similar to the radiation-collecting device 54 of the embodiment in FIG. 1. Compared with the embodiment of FIG. 1, the mirror 62 in FIG. 3 is the radiation-shift element, which has the center 621 distant from the optical axis 34 of the radiation-illuminating device 52. In this embodiment, the center 691 of the first beam splitter 69 is aligned with the optical axes 32 and 34. The radiation 44 and 45 are transmitted onto the center 691 of the first beam splitter 69 and then directed by the first beam splitter 69 along the optical axis 34 to the mirror 62. The center 621 of the mirror 62 is distant from the radiation 44 and 45 projected thereto. The mirror 62 in turn reflects the radiation 44 and 45 to the objective lens 73. The radiation 44 and 45 are translated from the optical axis 30 and the lens axis 731 of the objective lens 73. The lens axis 731, in this embodiment, is co-linear with the optical axis 30. The lens 73 then focuses the radiation 44 and 45 obliquely with respect to the lens axis 731 thereof onto the particles 20. The back-scattered radiation 40 and the fluorescence radiation 47 are collected and detected in a manner similar to the embodiment of FIG. 1, and the noise radiation 42 is also filtered in a manner similar to the embodiment of FIG. 1. The lens 84, the beam splitters 75 and 77 are aligned with the fluorescence radiation 47 from the first beam splitter 69 to collect the fluorescence radiation 47.

Figure 4:
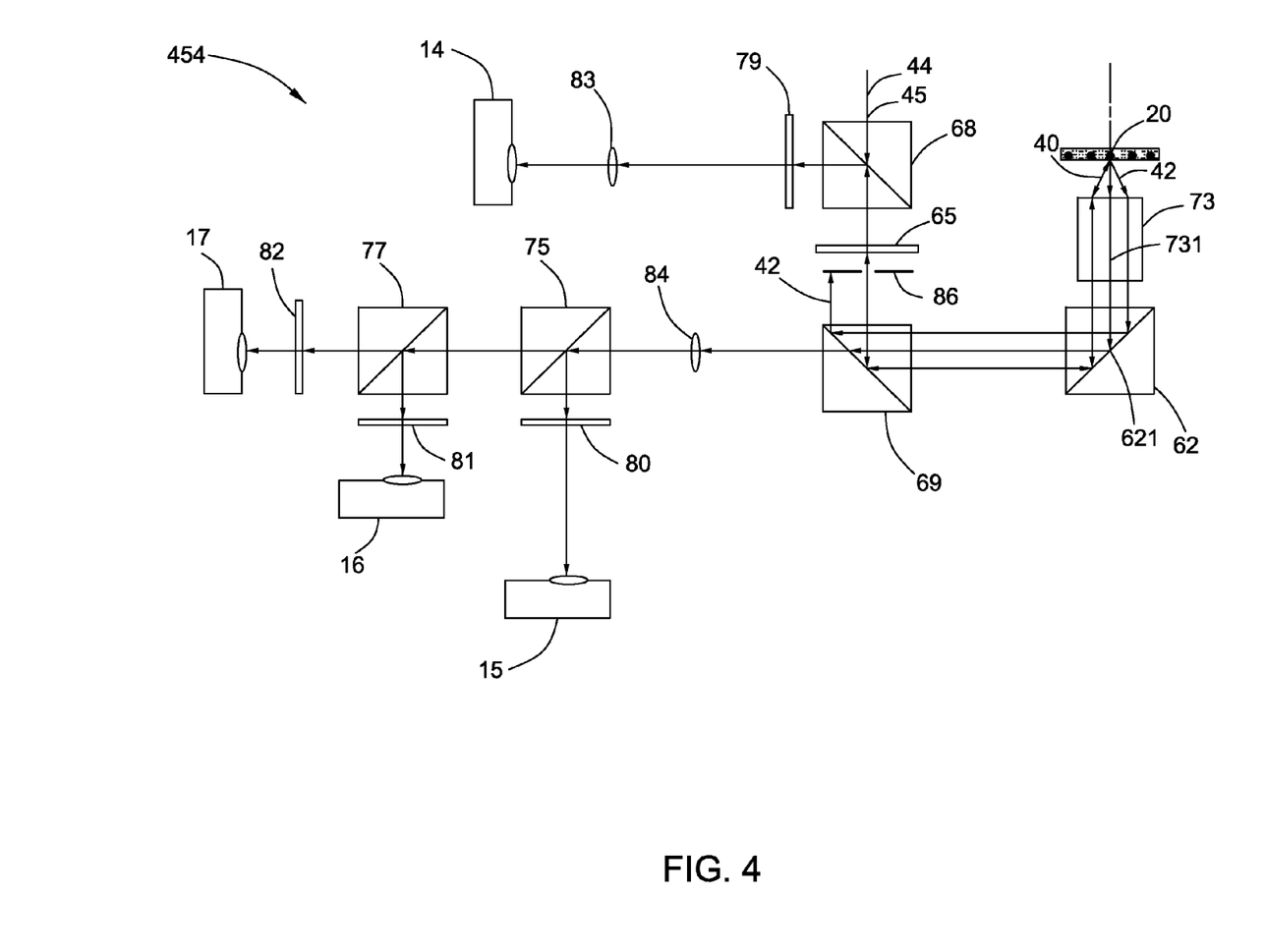
FIG. 4 is a schematic view of a radiation-collecting device in accordance with another exemplary embodiment.

FIG. 4 illustrates a schematic view of a radiation-collecting device 454 in accordance with another exemplary embodiment. The radiation-collecting device 454 in this embodiment may be operated in a manner similar to the radiation-collecting device 354 of the embodiment in FIG. 3. Compared with the embodiment of FIG. 3, the radiation limiting element 86 in FIG. 4 is located between the beam splitter 68 and the first beam splitter 69. The radiation limiting element 86 in FIG. 4 may be located at a position similar to the embodiment of FIG. 2. The radiation limiting element 86 is located and dimensioned to allow the radiation 44, 45 and the back-scattered radiation 40 passing through and block the noise radiation 42.

Figure 5:
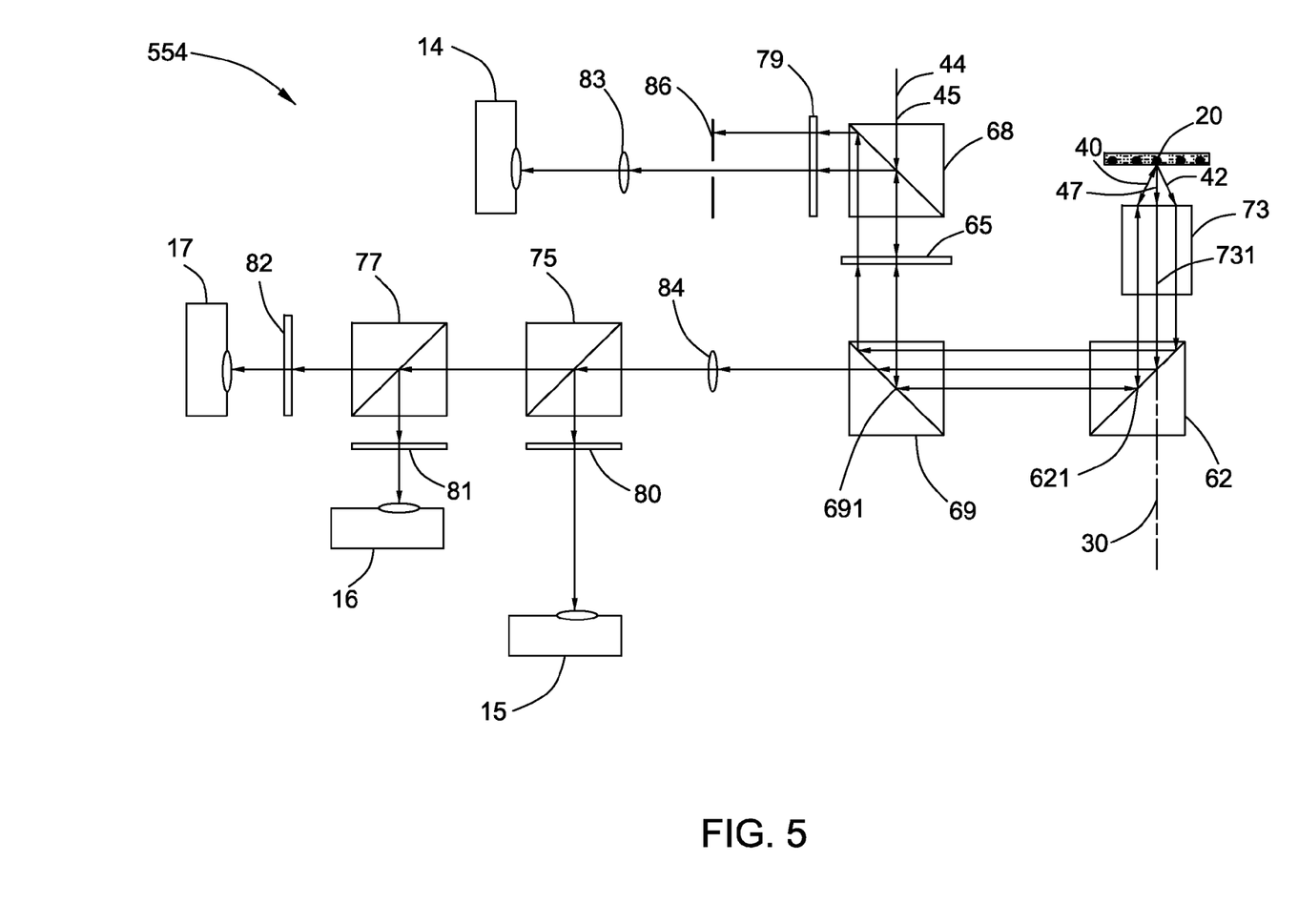
FIG. 5 is a schematic view of a radiation-collecting device in accordance with another exemplary embodiment.

FIG. 5 illustrates a schematic view of a radiation-collecting device 554 in accordance with another exemplary embodiment. The radiation-collecting device 554 in this embodiment may be operated in a manner similar to the radiation-collecting device 354 of the embodiment in FIG. 3. Compared with the embodiment of FIG. 3, the center 621 of the mirror 62 in FIG. 5 is distant from the optical axis 30 to translate the radiation 44 and 45 from the optical axis 30. In this embodiment, the center 621 of the mirror 62 is aligned with the center 691 of the first beam splitter 69. The radiation 44 and 45 from the first beam splitter 69 are transmitted onto the center 621 of the mirror 62 that in turn reflects the radiation 44 and 45 to the objective lens 73. The radiation 44 and 45 is translated from the lens axis 731 of the objective lens 73 which is co-linear with the optical axis 30. The objective lens 73 focuses the radiation 44 and 45 obliquely with respect to the lens axis 731 thereof onto the particles 20. The back-scattered radiation 40 and the fluorescence radiation 47 are collected and detected in a manner similar to the embodiment of FIG. 1, and the noise radiation 42 is also filtered in a manner similar to the embodiment of FIG. 1.

Figure 6:
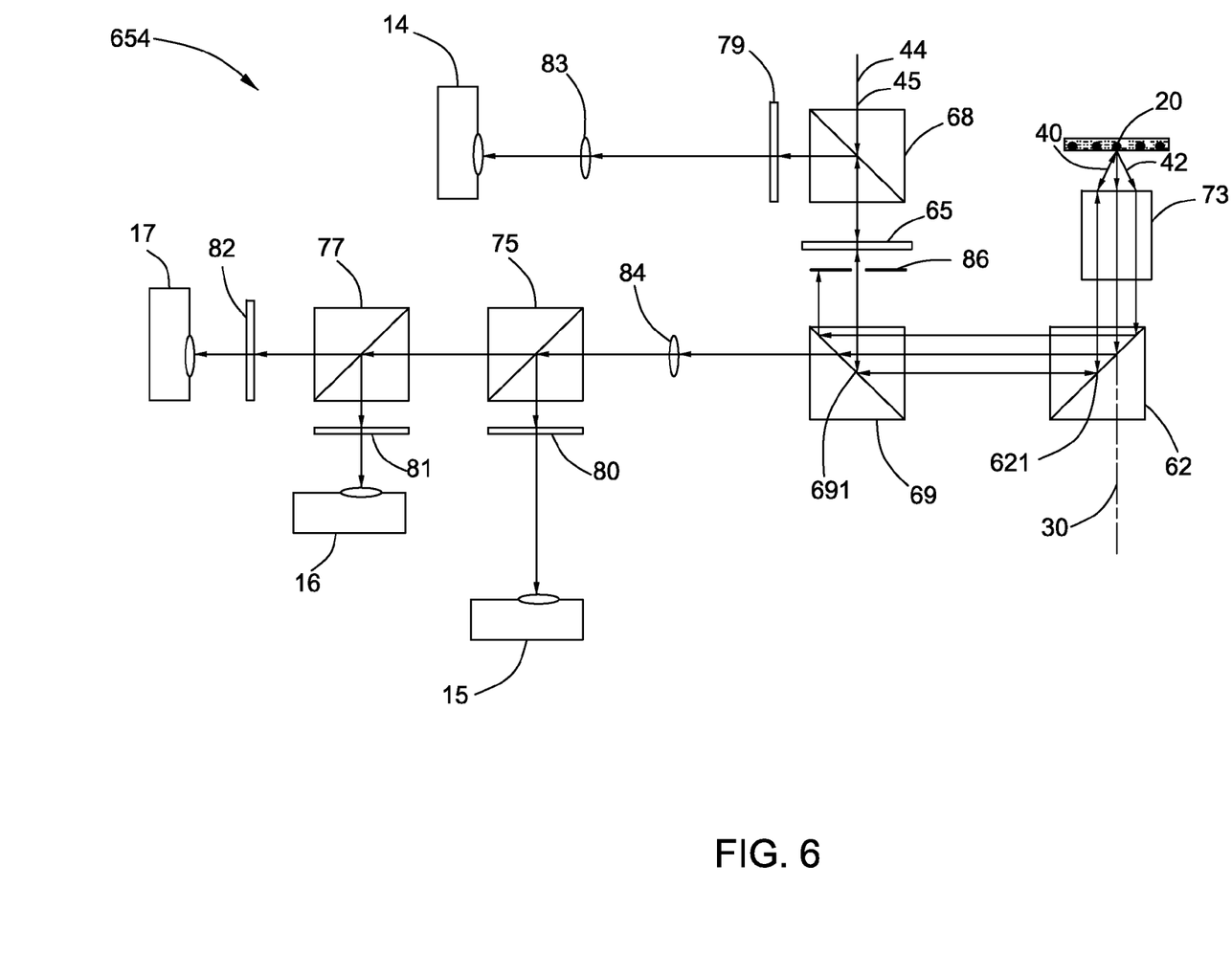
FIG. 6 is a schematic view of a radiation-collecting device in accordance with another exemplary embodiment.

FIG. 6 illustrates a schematic view of a radiation-collecting device 654 in accordance with another exemplary embodiment. The radiation-collecting device 654 in this embodiment may be operated in a manner similar to the radiation-collecting device 554 of the embodiment in FIG. 5. Compared with the embodiment of FIG. 5, the radiation limiting element 86 in FIG. 6 is located between the beam splitter 68 and the first beam splitter 69. The radiation limiting element 86 in FIG. 6 may be located at a position similar to the embodiment of FIG. 2. The radiation limiting element 86 is located and dimensioned to allow the radiation 44, 45 and the back-scattered radiation 40 passing through and block the noise radiation 42.

In some embodiments, both of the first beam splitter 69 and the mirror 62 are respectively distant from one or more of the optical axes of the optical system 12 to translate the radiation 44 and 45 from the lens axis 731 of the objective lens 73. In some embodiments, one of the first beam splitter 69 and the mirror 62 is distant from two or more of the optical axes of the optical system. In some embodiments, only one of the first beam splitter 69 and the mirror 62 is utilized.

Figure 7:
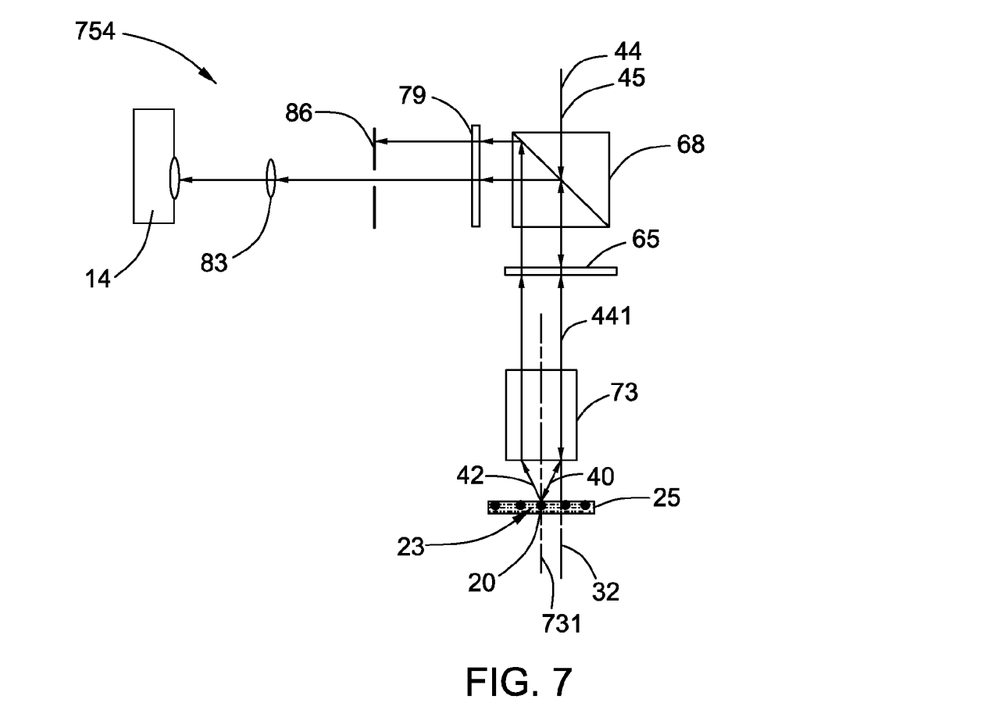
FIG. 7 is a schematic view of a radiation-collecting device in accordance with another exemplary embodiment.

FIG. 7 illustrates a schematic view of a radiation-collecting device 754 in accordance with another exemplary embodiment. In this embodiment, the radiation 44 and 45 from the beam splitter 68 pass through the wave plate 65 to the objective lens 73. The beam axis 441 of the radiation 44 and 45 projected to the objective lens 73 is co-linear with the optical axis 32. The lens axis 731 of the objective lens 73 is translated from the beam axis 441 and the optical axis 32. The center of the interrogation zone 23 is substantially aligned with the lens axis 731. The objective lens 73 focuses the radiation 44 and 45 obliquely onto the particle 20 at the center of the interrogation zone 23. The back-scattered radiation 40 and the noise radiation 42 are spatially separated from each other and emitted through the objective lens 73 and the wave plate 65 to the beam splitter 68 that in turn reflects the back-scattered radiation 40 and the noise radiation 42. The back-scattered radiation 40 is collected and detected in a manner similar to the embodiment of FIG. 1, and the noise radiation 42 is filtered in a manner similar to the embodiment of FIG. 1. In this embodiment, the radiation limiting element 86 is located downstream from the beam splitter 68. The radiation limiting element 86 may be located downstream or upstream from the filter 79. In this embodiment, the radiation 44 and 45 illuminate the particles 20 from the top side of the chip 25 and the back-scattered radiation 40 is also collected from the top side of the chip 25. In some embodiments, the radiation 44 and 45 illuminate the particles 20 form a lateral side of the chip 25 which extends vertically, and the back-scattered radiation 40 is also collected from the lateral side.

Figure 8:
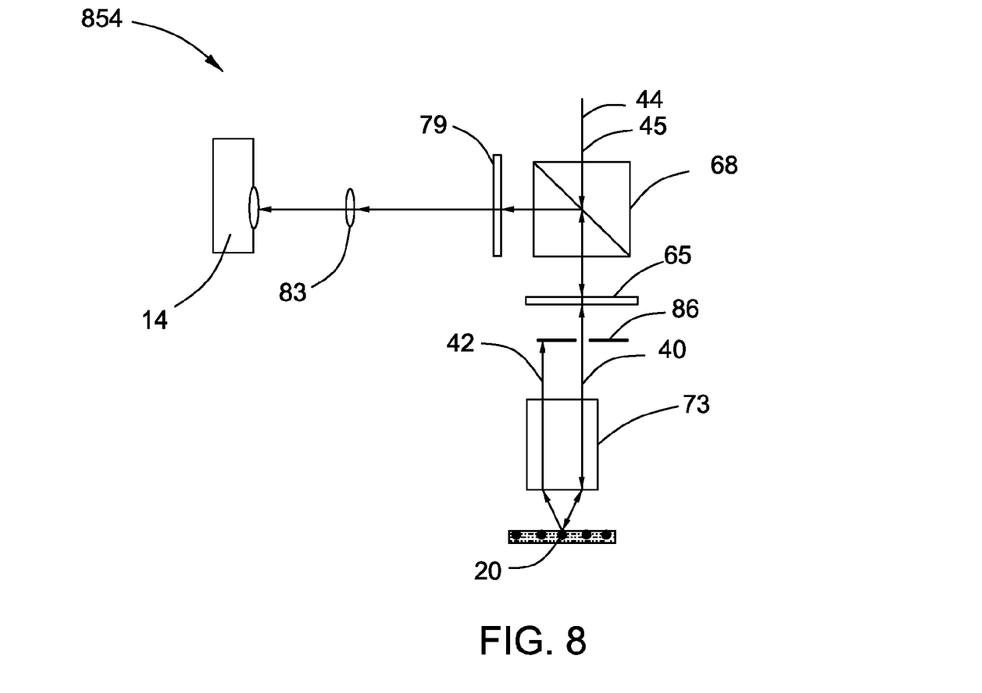
FIG. 8 is a schematic view of a radiation-collecting device in accordance with another exemplary embodiment.

FIG. 8 illustrates a schematic view of a radiation-collecting device 854 in accordance with another exemplary embodiment. The radiation-collecting device 854 in this embodiment may be operated in a manner similar to the radiation-collecting device 754 of the embodiment in FIG. 7. Compared with the embodiment of FIG. 7, the radiation limiting element 86 in FIG. 7 is located between the beam splitter 68 and the objective lens 73. The radiation limiting element 86 is located and dimensioned to allow the radiation 44, 45 and the back-scattered radiation 40 passing through and block the noise radiation 42.

Figure 9:
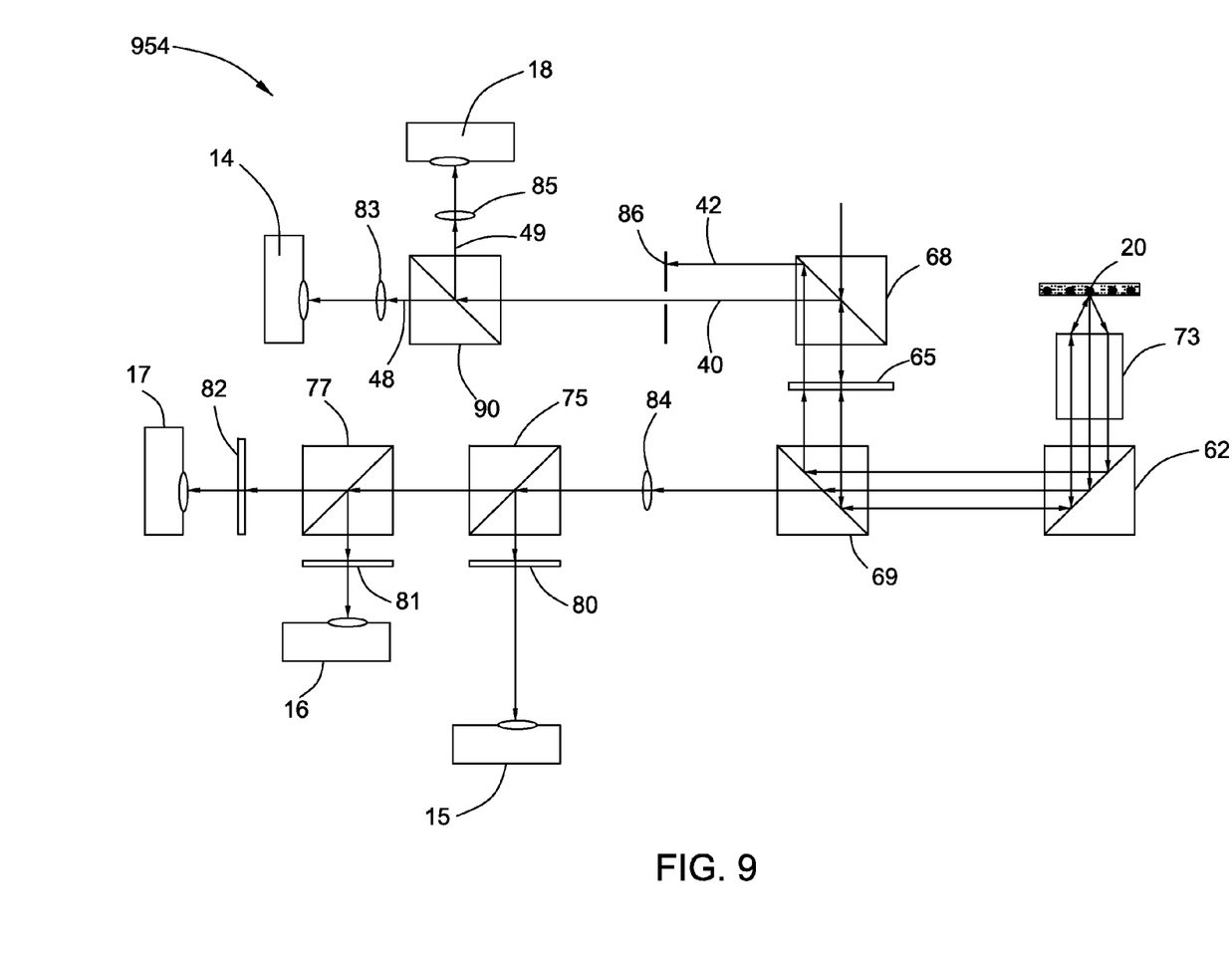
FIG. 9 is a schematic view of a radiation-collecting device in accordance with another exemplary embodiment.

FIG. 9 illustrates a schematic view of a radiation-collecting device 954 in accordance with another exemplary embodiment. Compared with the embodiment of FIG. 1, the radiation-collecting device 954 in FIG. 9 further includes a second beam splitter 90, a detector 18 and a lens 85. The back-scattered radiation 40 having two or more wavelength components are directed to the second beam splitter 90 that separates the back-scattered radiation 40 into back-scattered branching beams 48 and 49 at different wavelengths. The back-scattered branching beams 48 and 49 are respectively focused via the lenses 83 and 85 onto the detectors 14 and 18 to obtain different information of the particles 20. The second beam splitter 90 may be a dichroic beam splitter. In this embodiment, the back-scattered radiation 40 includes the red back-scattered radiation detected by the detector 14 and the green back-scattered radiation detected by the detector 18. The detector 18 may be a photo detector or an array of photo detectors or some other device. The second beam splitter 90, the detector 18 and the lens 85 may be utilized in the embodiments of FIGS. 2 to 8.

Figure 10:
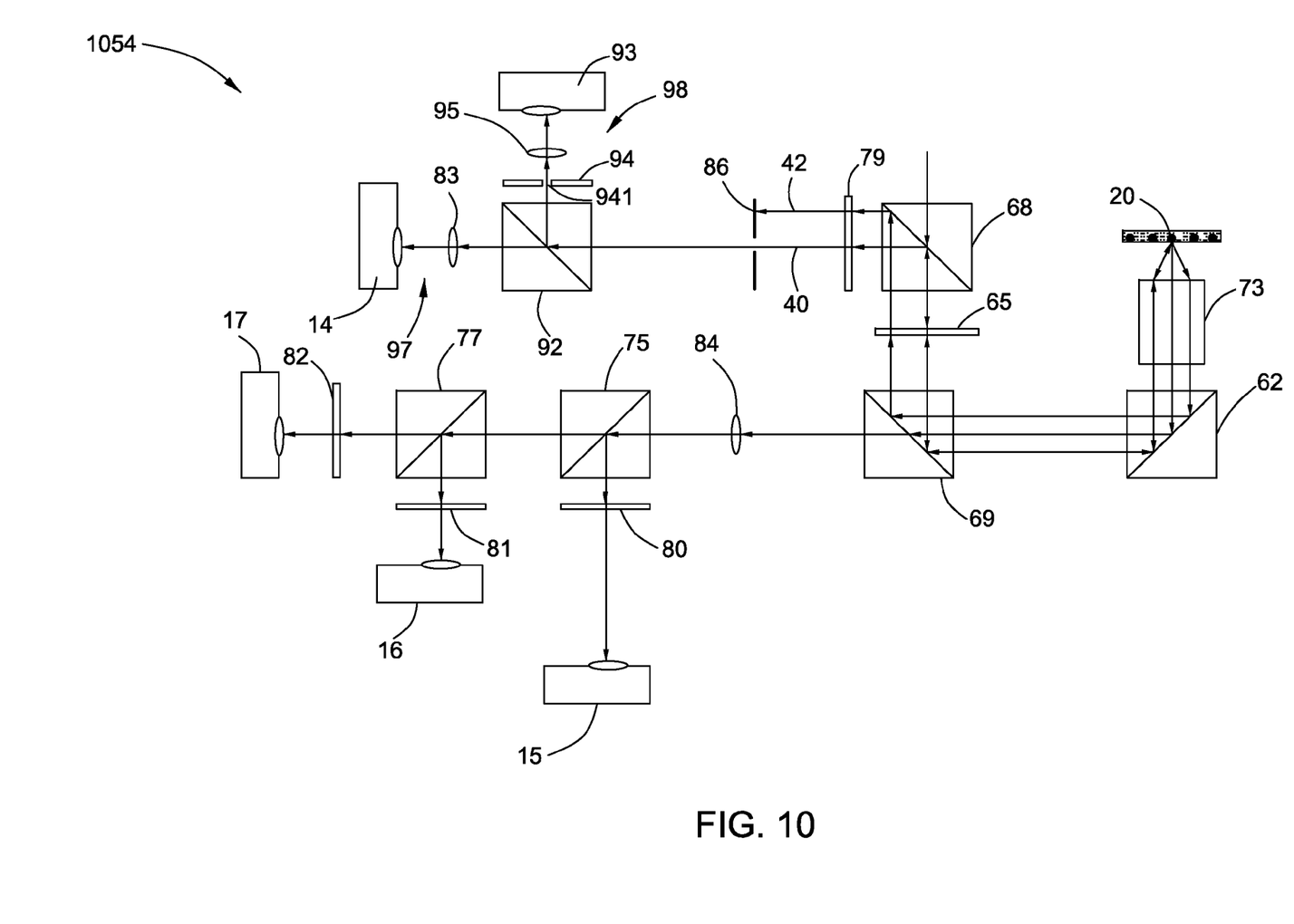
FIG. 10 is a schematic view of a radiation-collecting device in accordance with another exemplary embodiment.

FIG. 10 illustrates a schematic view of a radiation-collecting device 1054 in accordance with another exemplary embodiment. Compared with the embodiment of FIG. 1, the radiation-collecting device 1054 in FIG. 10 further includes a third beam splitter 92, a detector 93, a spatial filter 94 and a lens 95. The back-scattered radiation 40 at a single wavelength is directed to the third beam splitter 92 that splits the back-scattered radiation 40 into paths 97 and 98. The back-scattered radiation 40 may be split equally between the two paths 97 and 98. The spatial filter 94 is positioned in one of the paths 97 and 98 and includes an aperture 941 allowing the back-scattered radiation 40 within the aperture 941 to pass through. In this embodiment, the spatial filter 94 is positioned in the path 98. In another embodiment, the spatial filter 94 may be positioned in the path 97. In yet another embodiment, two different spatial filters are respectively provided in the paths 97 and 98.

The back-scattered radiation 40 propagating along the path 97 is focused by the lens 83 onto the detector 14. The back-scattered radiation 40 propagating along the path 98 is spatial filtered by the spatial filter 94. The back-scattered radiation 40 within the aperture 941 is passed to the lens 95 that in turn focuses the back-scattered radiation 40 onto the detector 93. The detector 93 may be a photo detector or an array of photo detectors or some other device. Distribution information of the particle 20 may be obtained through the detectors 14 and 93. The third beam splitter 92, the detector 93, the spatial filter 94 and the lens 85 may be also utilized in the embodiments of FIGS. 2 to 8. In some embodiments, the back-scattered radiation 40 is detected respectively by different detectors to obtain different information of the particles 20. In some embodiments, the back-scattered radiation 40 may be separated into more than two paths to be detected individually.

Figure 11:
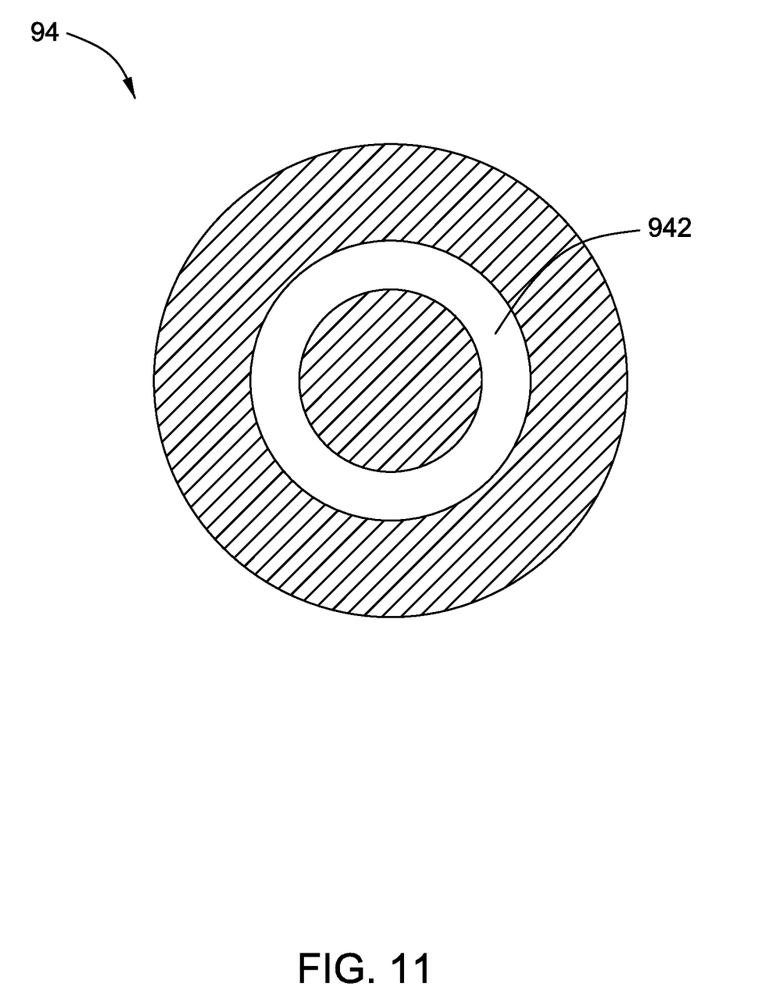
FIG. 11 is a top view of a spatial filter of a radiation-collecting device in accordance with an exemplary embodiment.

FIG. 11 illustrates a top view of the spatial filter 94 in accordance with an exemplary embodiment. In the illustrated embodiment, the spatial filter 94 includes a ring-shaped aperture 942 through which the back-scattered radiation 40 is projected onto the detector 93. In some embodiments, the aperture of the spatial filter 94 may be in the form of a circle, a portion of a ring, a sector, or in any other forms according to the applications.

Figure 12:
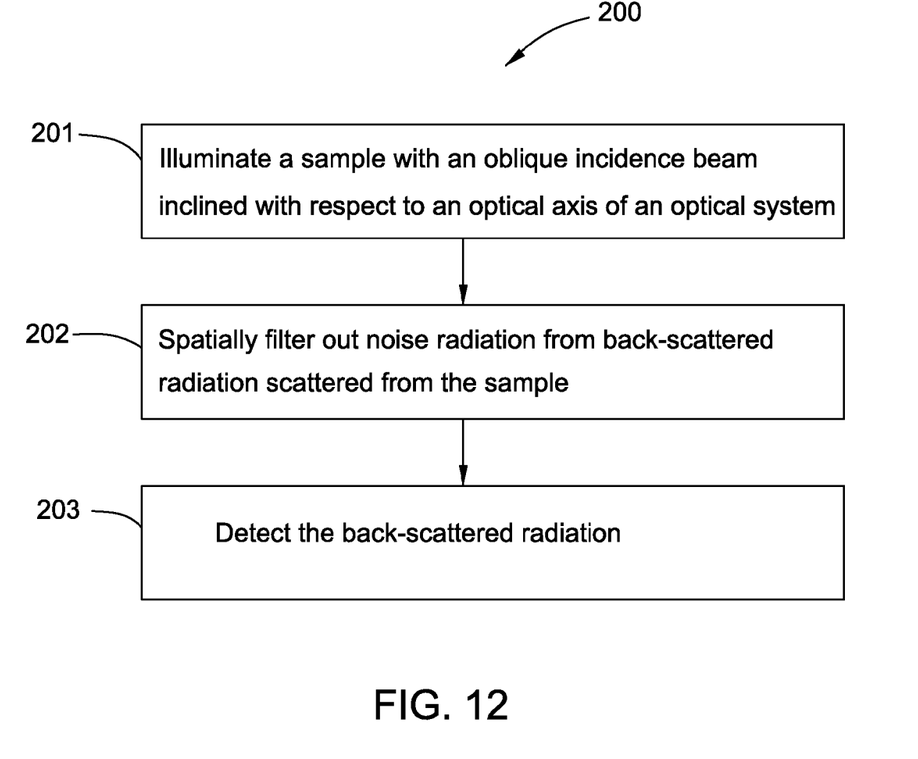
FIG. 12 is a flowchart of a method in accordance with an exemplary embodiment.

FIG. 12 illustrates a flowchart of a method 200 in accordance with an exemplary embodiment. The method 200 includes steps 201-203. At the step 201, a sample is illuminated with an oblique incidence beam which is inclined with respect to an optical axis of an optical system. The sample may include particles, such as fluorescent beads, shown in FIGS. 1 to 10. The oblique incidence beam may include one or more wavelength components. At step 202, noise radiation is spatially filtered out from back-scattered radiation. The back-scattered radiation is scattered backwardly from the sample illuminated by the oblique incidence beam. The back-scattered radiation is redirected along the oblique incidence beam. The scattering wavelength of the back-scattered radiation is the same as the excitation wavelength of the incidence beam. The noise radiation is mainly caused by a chip holding the sample. The chip, such as the chip 25 in FIGS. 1 to 10, reflects the oblique incidence beam on the outer surface and the interfaces thereof, so that the noise radiation is spatially separated from the back-scattered radiation. The noise radiation may be spatially filtered by the radiation limiting element 86 of FIGS. 1 to 10, detectors including filters, or any other elements capable of filtering radiation.

At step 203, the back-scattered radiation is detected. The back-scattered radiation may be detected by the detector 14, 18, 93 in FIGS. 1 to 10. The intensity of the back-scattered radiation detected at one or more different wavelengths is analyzed to derive selected information regarding to one or more particle types. Such information may include, for example, differentiation of the particle type relative to other particle types present in the sample, a relative or an absolute count of that particle type. In some embodiments, the back-scattered radiation is separated into back-scattered branching beams at different wavelengths, and the back-scattered branching beams are detected individually. Different information of the particle may be obtained regarding to the back-scattered branching beams at different wavelengths. In some embodiments, the back-scattered radiation is split into paths, and the back-scattered radiation along the paths is detected individually within individual spatial regions. The back-scattered radiation within different spatial regions may be analyzed to obtain the distribution information of the particle.

Figure 13:
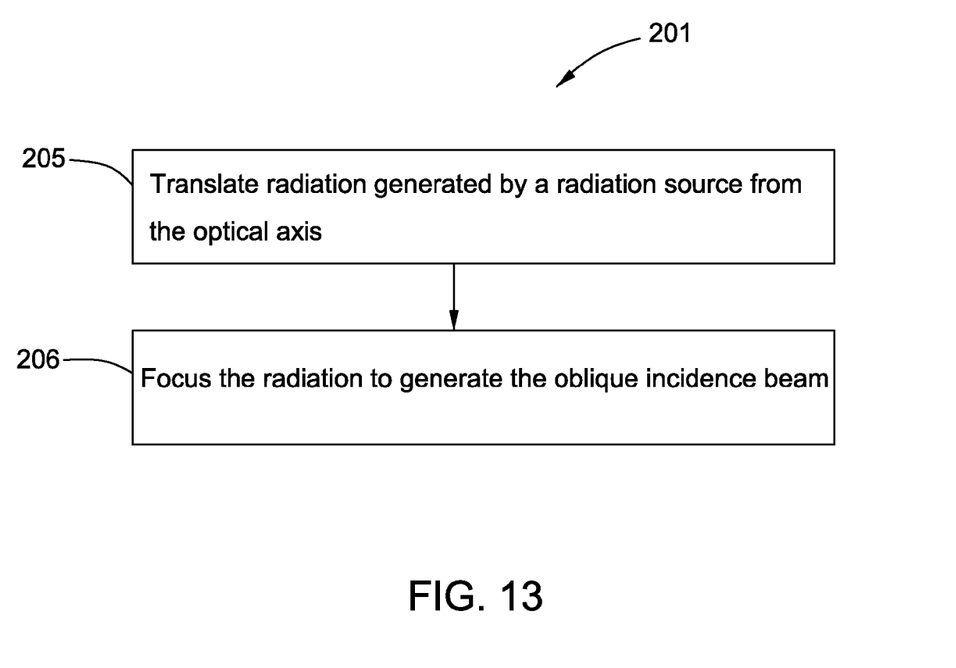
FIG. 13 is a flowchart illustrating the illuminating step of the method shown in FIG. 12 in accordance with an exemplary embodiment.

FIG. 13 illustrates a flowchart of the step 201 in accordance with an exemplary embodiment. The step 201 includes sub-steps 205 and 206. At the sub-step 205, radiation generated by one or more radiation sources is translated from the optical axis. The radiation may include one or more wavelength components. The radiation source may be the radiation source 50, 51 in FIG. 1. The radiation may be translated by the optical system 12 of FIGS. 1 to 8. The radiation is translated from the lens axis 731 of the objective lens 73 in FIGS. 1 to 8. At the sub-step 206, the radiation is focused on the sample to generate the oblique incidence beam. The radiation is converged onto the particle aligned with the optical axis. The radiation may be focused by the objective lens 73 in FIGS. 1 to 10 and the oblique incidence beam is inclined with respect with the lens axis 731 of the objective lens 73.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An optical system, comprising:
   a radiation source configured to generate radiation transmitted forwardly;
   a radiation-illuminating device optically coupled to the radiation source and configured to direct and focus the radiation obliquely with respect to an optical axis thereof onto a sample in a flow cell of a chip; and
   a radiation-collecting device configured to collect back-scattered radiation scattered from the sample and spatially separated from noise radiation back-reflected from the chip allowing the sample to flow through; and
   wherein the radiation-illuminating device comprises an objective lens having a lens axis translated laterally and parallelly from a beam axis of the radiation projected thereto and configured to focus the radiation obliquely with respect to the lens axis onto the sample.

2. The optical system of claim 1, wherein the radiation-collecting device comprises a radiation limiting element comprising an aperture allowing the back-scattered radiation to pass through to spatially filter out the noise radiation from the back-scattered radiation.

3. The optical system of claim 1, wherein the radiation-illuminating device comprises:
   a radiation-shift element optically coupled to the radiation source, the radiation-shift element having a center distant from the optical axis of the radiation-illuminating device to translate the radiation from the optical axis; and
   an objective lens optically coupled to the radiation-shift element and configured to focus the radiation from the radiation-shift element obliquely with respect to the optical axis onto the sample.

4. The optical system of claim 3, wherein the radiation-shift element comprises a first beam splitter configured to translate the radiation from the optical axis and separate the back-scattered radiation and fluorescence radiation from the sample, the first beam splitter having the center distant from the optical axis of the radiation-illuminating device.

5. The optical system of claim 3, wherein the radiation-shift element comprises a mirror having the center distant from the optical axis of the radiation-illuminating device.

6. The optical system of claim 1, wherein the radiation-collecting device comprises a second beam splitter configured to separate the back-scattered radiation into back-scattered branching beams at different wavelengths.

7. The optical system of claim 1, wherein the radiation-collecting device comprises:
   a third beam splitter configured to split the back-scattered radiation into a plurality of paths; and a spatial filter positioned in one of the plurality of paths and comprising an aperture allowing the back-scattered radiation within the aperture to pass through.

8. An apparatus comprising:
an optical system configured to illuminate forwardly a sample in a flow cell of a chip obliquely with respect to an optical axis thereof and spatially separate noise radiation from back-scattered radiation scattered from the sample, the noise radiation being back-reflected from the chip allowing the sample to flow through; and
a detector optically coupled to the optical system to detect the back-scattered radiation from the optical system; and
wherein the optical system comprises an objective lens having a lens axis translated laterally and parallelly from a beam axis of the radiation projected thereto and configured to focus the radiation obliquely with respect to the lens axis thereof onto the sample.

9. The apparatus of claim 8, wherein the optical system comprises,
a radiation source configured to generate radiation;
a radiation-illuminating device optically coupled to the radiation source and configured to direct and focus the radiation obliquely with respect to the optical axis thereof onto the sample; and
a radiation-collecting device configured to collect the back-scattered radiation.

10. The apparatus of claim 9, wherein the radiation-collecting device comprises a radiation limiting element comprising an aperture allowing the back-scattered radiation to pass through to spatially filter out the noise radiation from the back-scattered radiation.

11. The apparatus of claim 9, wherein the radiation-illuminating device comprises:
a radiation-shift element optically coupled to the radiation source, the radiation-shift element having a center distant from the optical axis of the radiation-illuminating device to translate the radiation from the optical axis; and
an objective lens optically coupled to the radiation-shift element and configured to focus the radiation from the radiation-shift element obliquely with respect to the optical axis onto the sample.

12. The apparatus of claim 11, wherein the radiation-shift element comprises a first beam splitter configured to translate the radiation from the optical axis and separate the back-scattered radiation and fluorescence radiation from the sample, the first beam splitter having the center distant from the optical axis of the radiation-illuminating device.

13. The apparatus of claim 11, wherein the radiation-shift element comprises a mirror having the center distant from the optical axis of the radiation-illuminating device.

14. The apparatus of claim 8, wherein the detector comprises a multi-element detector.

15. A method comprising:
illuminating forwardly a sample in a flow cell of a chip with an oblique incidence beam inclined with respect to an optical axis of an optical system;
spatially filtering out noise radiation from back-scattered radiation scattered from the sample, the noise radiation being back-reflected from the chip allowing the sample to flow through; and
detecting the back-scattered radiation; and
wherein illuminating forwardly the sample comprises laterally and parallelly translating radiation generated by one or more radiation sources from the optical axis and focusing the radiation on the sample to generate the oblique incidence beam.

16. The method of claim 15, wherein detecting the back-scattered radiation comprises separating the back-scattered radiation into back-scattered branching beams with different wavelengths and detecting individually the back-scattered branching beams.

17. The method of claim 15, wherein detecting the back-scattered radiation comprises splitting the back-scattered radiation into a plurality of paths and detecting individually the back-scattered radiation along the plurality of paths within individual spatial regions.

* * * * *

UNITED STATES PATENT AND TRADEMARK OFFICE
CERTIFICATE OF CORRECTION

| | |
|---|---|
| PATENT NO. | : 8,994,941 B2 |
| APPLICATION NO. | : 13/687374 |
| DATED | : March 31, 2015 |
| INVENTOR(S) | : Shi |

Page 1 of 1

It is certified that error appears in the above-identified patent and that said Letters Patent is hereby corrected as shown below:

In the Specification

In Column 1, Line 8, delete "N00173-08-2-0003" and insert -- N00173-08-2-C003 --, therefor.

In Column 1, Line 9, delete "Navel" and insert -- Naval --, therefor.

In the Claims

In Column 11, Line 19, in Claim 9, delete "comprises," and insert -- comprises: --, therefor.

Signed and Sealed this
Twenty-ninth Day of September, 2015

Michelle K. Lee
*Director of the United States Patent and Trademark Office*